United States Patent
Kitamura et al.

(10) Patent No.: US 6,326,512 B1
(45) Date of Patent: Dec. 4, 2001

(54) METHOD OF PRODUCING AN OPTICALLY ACTIVE β-HYDROXY SULFONIC ACID COMPOUND BY CATALYTIC ASYMMETRIC HYDROGENATION

(75) Inventors: Masato Kitamura, Nagoya; Masahiro Yoshimura, Kasugai; Naoki Kanda, Okazaki; Ryoji Noyori, Nisshin, all of (JP)

(73) Assignee: President of Nagoya University, Nagoya (JP)

( * ) Notice: Subject to any disclaimer, the term of this patent is extended or adjusted under 35 U.S.C. 154(b) by 0 days.

(21) Appl. No.: 09/584,747

(22) Filed: Jun. 1, 2000

(30) Foreign Application Priority Data

Dec. 2, 1999 (JP) .................................. 11-343921

(51) Int. Cl.$^7$ .......................... C07C 309/00; C07C 29/14
(52) U.S. Cl. .......................... 562/108; 562/30; 562/109; 568/881
(58) Field of Search .................... 562/108, 109, 562/30; 568/881

(56) References Cited

U.S. PATENT DOCUMENTS 5,066,815 * 11/1991 Sayo et al. .
5,508,435 *  4/1996 Armstrong et al. .
5,532,402 *  7/1996 Noyori et al. .

OTHER PUBLICATIONS

M. Kitamura, et al., 75th Symposium on Organic Synthesis, Japan, 5 pages, Jun. 2, 1999.
M. Kitamura, et al, Tetrahedron, vol. 55, pp. 8769–8785, "Asymmetric Synthesis of β–Hydroxy Sulfonic Acids by Binap/Ru–Catalyzed Hydrogenation", 1999.
M. Kitamura, et al., Enantiomer, vol. 1, pp. 281–303, "Synthesis of α–Amino Phosphonic Acids by Asymmetric Hydrogenation", 1996.
R. Noyori, et al., Bulletin of the Chemical Society of Japan, vol. 68, No. 1, pp. 36–55, "Stereoselective Organic Synthesis Via Dynamic Kinetic Resolution", 1995.

(List continued on next page.)

*Primary Examiner*—Paul J. Killos
*Assistant Examiner*—Mahreen Chaudhry
(74) *Attorney, Agent, or Firm*—Oblon, Spivak, McClelland, Maier & Neustadt, P.C.

(57) ABSTRACT

Disclosed is a method of producing an optically active β-hydroxy sulfonic acid compound comprising hydrogenating a β-keto sulfonic acid compound represented by formula 1:

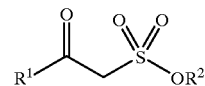

where $R^1$ represents an alkyl or a phenyl group, which may be substituted, and $R^2$ represents sodium or an alkyl group, in an acidic solvent, in the presence of an asymmetric catalyst comprising a complex of bivalent Ru, having 2,2'-bis(diphenylphosphino)-1,1'-binaphthyl as a ligand, to produce a compound represented by formula 2:

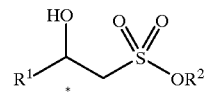

where $R^1$ and $R^2$ are as defined above, and * designates an asymmetric carbon atom.

8 Claims, 1 Drawing Sheet

OTHER PUBLICATIONS

M. Kitamura, et al., Tetrahedron Letters, vol. 36, No. 32, pp. 5769–5772, "Asymmetric Synthesis of α–Amino β–Hydroxy Phosphonic Acids Via Binap–Ruthenium Catalyzed Hydrogenation", 1995.

M. Kitamura, et al., American Chemical Society, vol. 117, No. 10, pp. 2931–2932, "Asymmetric Hydrogenation of β–Keto Phosphonates: A Practical Way to Fosfomycin", 1995.

M. Kitamura, et al., Organic Syntheses, vol. 71, No. 1, pp. 1–13, "Asymmetric Hydrogenation of 3–Oxo Carboxylates Using Binap–Ruthenium Complexes: (R)–(–)–Methyl 3–Hydroxybutanoate", 1992.

W. D. Lubell, et al., Tetrahedron: Asymmetry, vol. 2, No. 7, pp. 543–554, "Enantioselective Synthesis of β–Amino Acids Based on Binap–Ruthenium (II) Catalyzed Hydrogenation", 1991.

M. Kitamura, et al., Tetrahedron Letters, vol. 32, No. 33, pp. 4163–4166, "Convenient Preparation of Binap–Ruthenium(II) Complexes Catalyzing Asymmetric Hydrogenation of Functionalized Ketones", 1991.

M. Kitamura, et al., Tetrahedron: Asymmetry, vol. 1, No. 1, pp. 1–4, "Dynamic Kinetic Resolution in Binap–Ruthenium(II) Catalyzed Hydrogenation of 2–Substituted 3–Oxo Carboxylic Esters", 1990.

R. Noyori, et al., Journal of the American Chemical Society, vol. 111, No. 25, pp. 9134–9135, "Stereoselective Hydrogenation Via Dynamic Kinetic Resolution", 1989.

M. Kitamura, et al., Tetrahedron Letters, vol. 29, No. 13, pp. 1555–1556, "A Practical Asymmetric Synthesis of Carnitine", 1988.

M. Kitamura, et al., Journal of the American Chemical Society, vol. 110, No. 2, pp. 629–631, "Homogeneous Asymmetric Hydrogenation of Functionalized Ketones", 1988.

R. Noyori, et al., Journal of the American Chemical Society, vol. 109, No. 19, pp. 5856–5858, "Asymmetric Hydrogenation of β–Keto Carboxylic Esters. A Practical, Purely Chemical Access to β–Hydroxy Esters in High Enantiomeric Purity", 1987.

* cited by examiner

METHOD OF PRODUCING AN OPTICALLY ACTIVE β-HYDROXY SULFONIC ACID COMPOUND BY CATALYTIC ASYMMETRIC HYDROGENATION

CROSS-REFERENCE TO RELATED APPLICATIONS

This application is based upon and claims the benefit of priority from the prior Japanese Patent Application No. 11-343921, filed Dec. 2, 1999, the entire contents of which are incorporated herein by reference.

BACKGROUND OF THE INVENTION

The present invention relates to an asymmetric producing method, and particularly a method of producing an optically active β-hydroxy sulfonic acid compound by catalytic asymmetric hydrogenation.

β-Hydroxy sulfonic acid compounds are among the important substances widely utilized in chemical industry and life science fields. For example, they are utilized as lubricants in electroplating of copper and Sn—Zn alloys and electrolytic pigmentation coating of aluminum, as stabilizers of disperse dyes, and as surface active ingredients of household cleansers. They also have high utility value as acid catalysts. Further, they attract attention in development of medicines based upon enzyme antagonism, since the sulfonyl group with a tetrahedrally arranged $sp^3$ sulfur atom antagonizes with carboxyl groups. Development of practical method of providing optically active compounds is required, since difference in chirality changes molecular assembly forms and greatly influence interface and bulk properties or characteristics and extent of biological activities.

Previously, reactions of epoxides or 1-chloro-2-alkanols with sodium sulfite and reduction of β-keto sulfonic acid compounds with metal hydrides have been reported as a method of producing a β-hydroxy sulfonic acid compound.

However, these previous methods described above can not form an optically active β-hydroxy sulfonic acid compound.

BRIEF SUMMARY OF THE INVENTION

The purpose of the present invention is to provide a method that can effectively produce an optically active β-hydroxy sulfonic acid compound in good asymmetric yield and chemical yield through simple operations.

The present inventors found that a kind of Ruthenium catalyst asymmetrically converts a β-keto sulfonic acid compound to an optically active β-hydroxy sulfonic acid compound in hydrogenation, as a result of repetition of wholehearted research paying attention to hydrogenation for solving the problem mentioned above, and completed the present invention.

Thus, the present invention provides a method of producing an optically active β-hydroxy sulfonic acid compound comprising hydrogenating a β-keto sulfonic acid compound represented by formula 1:

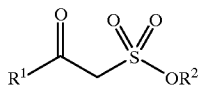

where $R^1$ represents an alkyl or a phenyl group, which may be substituted, and $R^2$ represents sodium or an alkyl, in an acidic solvent, in the presence of an asymmetric catalyst comprising a complex of bivalent Ru, having 2,2'-bis(diphenylphosphino)-1,1'-binaphthyl as a ligand, to produce a compound represented by formula 2:

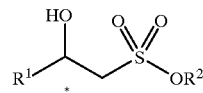

where $R^1$ and $R^2$ are as defined above, and * indicates an asymmetric carbon.

In the present invention, the Ru complex comprises $[RuCl_2((R)$ or $(S)$-binap$)]$, $[RuCl(C_6H_6)((R)$ or $(S)$-binap$)]$Cl, or $[Ru(CH_3COO)_2((R)$ or $(S)$-binap$)]$, where binap represents 2,2'-bis(diphenylphosphino)-1,1'-binaphthyl.

Further, in the present invention, the acidic solvent is preferably acidified with hydrochloric acid, and has a hydrochloric acid concentration in the range of 5 to 25 mmol/L.

Further, in the present invention, the solvent preferably comprises methanol, ethanol, or acetone.

According to the present invention, an optically active β-hydrox ysulfonic acid compound can be effectively produced by asymmetric hydrogenation under atmospheric pressure.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
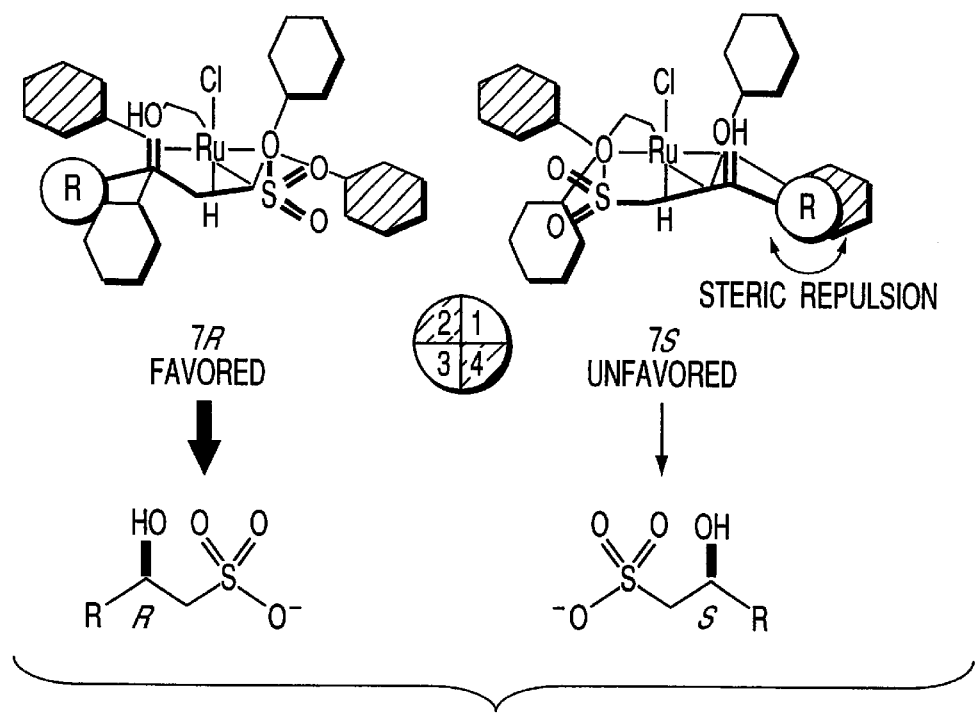
FIG. 1 shows a complex or a transition state $7_R$ and $7_S$ of (R)-binap-Ru monohydrido complex and a substrate that are in relation of a diastereomer with each other.

As described above, the present invention provides a new method of producing an optically active β-hydroxy sulfonic acid compound by catalytic asymmetric hydrogenation.

The catalyst in the present invention comprises a complex of bivalent Ru, having 2,2'-bis(diphenylphosphino)-1,1'-binaphthyl (to be written as binap hereinafter) as a ligand. In the present invention, (R)-binap-Ru dichloro complex $[RuCl_2((R)$-binap$)]$ represented by formula (R)-3:

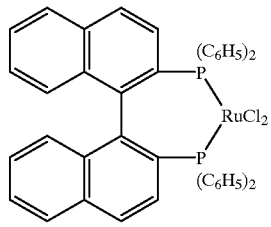

or (S)-binap-Ru dichloro complex [RuCl$_2$((S)-binap)] represented by formula (S)-3:

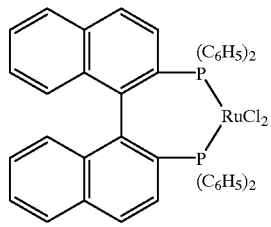

is preferably used. Said binap-Ru dichloro complex can be prepared by reacting [RuCl$_2$(C$_6$H$_6$)]$_2$ with binap in dimethylformamide (dmf) at 100° C. and then removing all the volatile substances (see J. Am. Chem. Soc. 1995, 117, 2931–2932), and the residual yellow solid can be used in hydrogenation of a β-keto sulfonic acid compound in the present invention. Further, a cationic Ru dichloro complex [RuCl(C$_6$H$_6$)((R) or (S)-binap)]Cl, a neutral Ru diacetato complex Ru(CH$_3$COO)$_2$[(R) or (S)-binap] can also preferably used as a catalyst for asymmetric synthesis of the present invention. Performance of the catalysts for asymmetric producing of the present invention is compared with hydrogenation reactions using a cationic Rh complex [Rh((R)-binap)(CH$_3$OH)$_2$]ClO$_4$ and a neutral Rh complex RhCl((R)-binap)(cod) in the following embodiments. As shown in Table 1 as the results, the present reaction hardly proceeds when using the cationic or neutral Rh complex, failing to yield the end product. Incidentally, selectivity of configuration of the formed β-hydroxy sulfonic acid compound is determined by the configuration of the ruthenium complex used.

The catalytic asymmetric hydrogenation reaction in the producing of a β-hydroxy sulfonic acid compound of the present invention can be shown by the following equation.

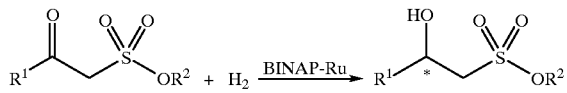

Here, R$^1$ represents an optionally substituted alkyl or phenyl group, such as a methyl group, an i-propyl group, n-heptadecyl group, or 4-n-octyl phenyl group, and R$^2$ represents sodium or an alkyl group such as an ethyl group.

Thus, in the present invention, a β-keto sulfonic acid compound represented by formula (1):

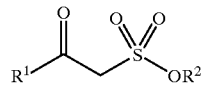

is used as the substrate, and the end product, an optically active β-hydroxy sulfonic acid compound, is obtained by hydrogenation of said β-keto sulfonic acid compound. Particularly, 1a having a phenyl group as R$^1$ in formula (1), 1b having a long chain alkyl group (n-C$_8$H$_{17}$) introduced to the phenyl group, 4-(n-C$_8$H$_{17}$)-C$_6$H$_4$, 1c which is CH$_3$, 1d which is n-C$_{15}$H$_{31}$, 1e which is i-C$_3$H$_7$, and ethyl sulfonate 4 in which R$^2$ is C$_2$H$_5$ can be preferably used as the β-keto sulfonic acid compound (the substrate).

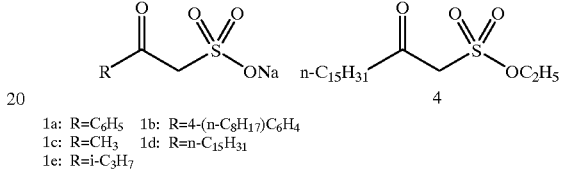

1a: R=C$_6$H$_5$  1b: R=4-(n-C$_8$H$_{17}$)C$_6$H$_4$
1c: R=CH$_3$  1d: R=n-C$_{15}$H$_{31}$
1e: R=i-C$_3$H$_7$

For example, the hydrogenation reaction of sodium 2-oxo-2-phenylethanesulfonate (the substrate) in the presence of [RuCl$_2$((R)-binap)] can be shown by the following equation.

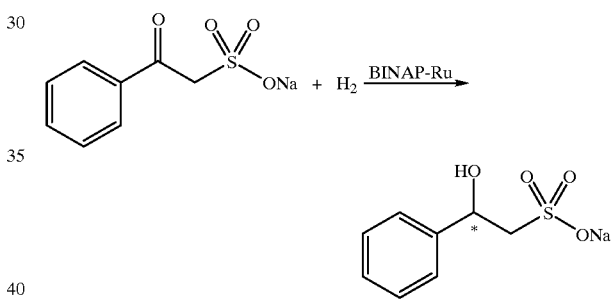

Said reaction is carried out by suspending a β-hydroxy sulfonic acid compound as the substrate, a binap-Ru complex as the catalyst, and an aqueous acid solution such as hydrochloric acid in a solvent such as methanol, and agitating the suspension under an atmosphere of hydrogen. Thus, the hydrogenation reaction of the present invention can be carried out only by exposing a solution of a β-hydroxy sulfonic acid compound in the presence of a binap-Ru complex and an acid to an atmosphere of hydrogen at the atmospheric pressure, and hydrogenation conditions such as acid concentration, reaction temperature and the kind of solvent can be adjusted to maintain high selectivity of both of the enantiomeric isomers and improve chemical yield easily.

As shown in the embodiments below, when [RuCl$_2$((R)-binap)]=0.5 mM, [sodium 2-oxo-2-phenylethanesulfonate]= 100 mM, hydrogen pressure 1 atm., solvent methanol, reaction temperature of 50° C. are taken as the standard condition, addition of HCl to said reaction system to a concentration of [HCl]=5 mM results in about ten times of acceleration effect of the reaction, and almost quantitative yield of (R)-2a in 96% enantiomeric excess (to be written ee below). Further, not only HCl but also strong acids such as H$_2$SO$_4$ and CF$_3$SO$_3$H can be preferably used.

Reaction path and the enantioface selection mechanism of the present invention will be discussed below in view of such an effect of addition of HCl. The hydrogenation reactions using binap-Ru complexes of the present invention probably proceed in a monohydride mechanism. The catalyst precursor, [RuCl$_2$(binap)], is present in the form of aggregates and partially dissociates into monomeric RuCl$_2$ (binap)S$_2$ influenced by donor molecules (S) such as solvents, substrates, and products. This splits a hydrogen molecule and turns into the monohydride A accompanied by elimination of HCl. It is important that the monohydride reversibly reacts with the substrate to form B, and the protonation stabilizes the transition state by increasing the electrophilicity of the carbon center. In an alcoholic system, C turns into the product and [RuCl(binap)Sn]$^+$, and the latter reacts with H$_2$ to regenerate A. Though HCl already exists in the reaction system, the amount is considered to be too small for hydrogenation to proceed easily. The reaction can be understood to have been accelerated as enough amount of H$^+$ was supplied by addition of strong acid. Alternatively, a route in which A is converted to D via B (not via C) as in hydrogenation of functionalized olefins can be considered as another possibility. The product and A are formed if alkoxy-Ru bond of D is hydrolyzed, and the product and [RuCl(binap)Sn]$^+$ are generated if D is decomposed by protonation. Addition of strong acid is also considered to have facilitated this decomposition by protonation.

A

RuHCl(binap)S$_2$

B

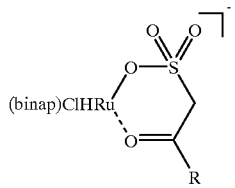

C

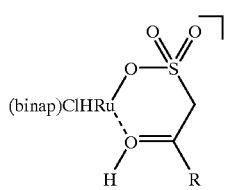

D

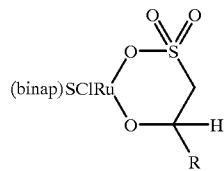

A complex or a transition state 7$_R$ and 7$_S$ of (R)-binap-Ru monohydride complex and the substrate in a diastereomeric relation as shown in FIG. 1 is assumed (the phosphorus atom on the Ru atom and the binaphthyl skeleton are omitted for simplicity). R compound is formed from 7$_R$, and S compound is formed from 7$_S$. Here, since large steric repulsion occurs in 7$_S$ between the substituent R and an equatorial benzene ring of the catalyst, reaction via 7$_R$ is preferred. High level steric complementation in the substrate-catalyst complex in 7$_R$ is shown to be important for enantioselectivity to occur.

Said hydrogenation reaction in the present invention is typically desirable to be carried out under following conditions.

Molar ratio: β-keto sulfonic acid compounds/Ru-binap complex=200/1 to 1000/1.

Reaction temperature: 25 to 80° C.

Hydrogen pressure: 1 to 100 atm., more preferably 1 to 10 atm.

Solvent: methanol, ethanol and acetone, more preferably methanol and ethanol

The method of the present invention efficiently produces an optically active β-hydroxy sulfonic acid compound.

EXAMPLES

Embodiments of the present invention are explained more precisely below. Each example of the present invention and each comparative example do not limit the present invention. Further, ee of the hydrogenation products in each example of the present invention and each comparative example were determined by $^1$HNMR analysis of the diastereomer ratio of an ester [(R,R)-5, (R,S)-5] prepared from formula 2a:

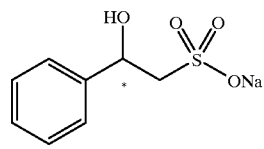

and (S)-3,3,3-trifluoro-2-methoxy-2-phenylpropanoyl chloride ((S)-MTPACl), and the absolute configuration were determined by X ray crystal structure analysis of formula 6.

(R,R)-5

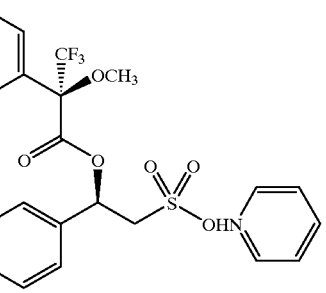

(R,S)-5

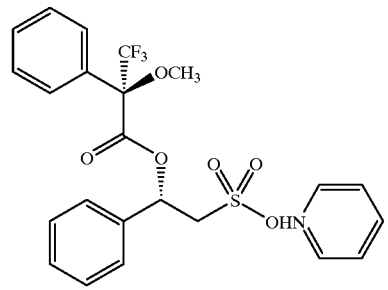

-continued

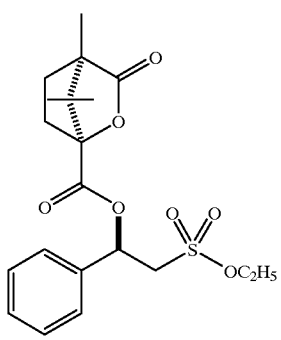

6

Figure 2:
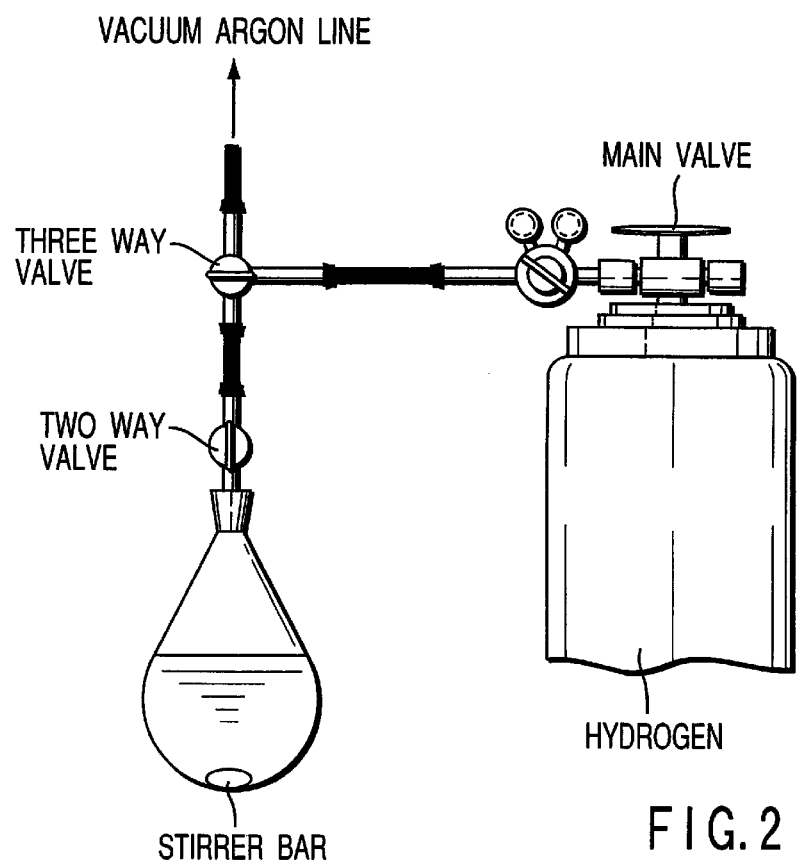
FIG. 2 shows an experimental apparatus for the catalytic hydrogenation method of the present invention.

Sodium 2-Oxo-2-phenylethanesulfonate (1a), [RuCl$_2$((R)-binap)], and degassed methanol were added to a 2 litter round bottom flask as shown in FIG. 2 to result in [(R)-3]= 0.5 mM and [1a]=100 mM. After evacuating the flask using a vacuum argon line, the flask was filled with hydrogen of atmospheric pressure through a hydrogen inlet tube. The flask was vigorously agitated at 50° C. for 20 hours. Table 1 shows the result of condition study below taking said condition, namely [(R)-3]=0.5 mM, [1a]=100 mM, hydrogen pressure 1 atm., methanol as the solvent, reaction temperature 50° C., as the standard.

Comparative Example 1

Reaction hardly proceeded in this comparative example wherein HCl did not exist in the reaction system (No. 1).

Comparative Example 2

(R)-2a was obtained in 96% ee by raising the hydrogen pressure as high as 100 atm., although conversion was 42% (No. 2).

Example 1

About ten-fold reaction acceleration effect was obtained by addition of HCl to reaction system No. 1 to result in [HCl]=5 mM, yielding (R)-2a almost quantitatively in 96% ee (No. 3).

Example 3

The reaction rate was still higher at HCl concentration [HCl]=25 mM completing the reaction in 3 hours (No. 5).

Example 4

Enantioface selectivity was not reduced by raising the reaction temperature to 80° C. (No. 6).

Example 5

The reaction completed in 72 hours even when the substrate concentration [1a] was raised to 1 M (No. 7).

Example 6

At temperature as high as 80° C., the amount of catalyst can be reduced to 1/1000 of the substrate though reaction takes much time (No. 8).

Examples 7, 8

Reaction acceleration effects similar to the case of addition of HCl to reaction systems were also observed with H$_2$SO$_4$ and CF$_3$SO$_3$H (Nos. 9, 10).

Examples 10–15

Though ethanol and acetone can be used except methanol, both reactivity and selectivity decreased when acetone was used. Reaction hardly proceeded in tetrahydrofuran (THF), benzene, dichloromethane, and acetonitrile (Nos. 12–17).

Examples 16, 17

In the presence of HCl, cationic binap-Ru dichloro complex and neutral binap-Ru diacetate complex can also be used as asymmetric synthesis catalysts in the present invention (Nos. 18, 20).

Comparative Examples 4, 5

When cationic and neutral binap-Rh complexes were used in the presence of HCl, reaction hardly proceeded (Nos. 21, 22)

Examples 18–22

Arylketone 1b (in formula (1), $R^1$=4-(n-C$_8$H$_{17}$)-C$_6$H$_4$, $R^2$=Na, No. 23), alkylketone 1c (in formula (1), $R^1$=CH$_3$, $R^2$=Na, No. 24), alkylketone 1d (in formula (1), $R^1$=n-C$_{15}$H$_{31}$, $R^2$=Na, No. 25), alkylketone 1e (in formula (1), $R^1$=i-C$_3$H$_7$, $R^2$=Na, No. 26), and ethyl sulfonate 4 (in formula (1), $R^1$=n-C$_{15}$H$_{31}$, $R^2$=C$_2$H$_5$, No. 27) were used as the substrate in place of sodium 2-oxo-2-phenylsulfonate (1a).

TABLE 1[a]

| No. | Substrate (mM) | Catalyst (mM) | Additive (mM) | Substrate/catalyst (mole ratio) | Solvent | Time (h) | Conversion (%) | Product ee (%) | Config-uration | Note |
|---|---|---|---|---|---|---|---|---|---|---|
| 1 | 1a(100) | RuCl$_2$[(R)-binap] [(R)-3)] (0.5) | — | 200 | CH$_3$OH | 20 | 9 | — | — | Comparative example 1 |
| 2[b] | 1a(100) | (R)-3 (0.5) | — | 200 | CH$_3$OH | 20 | 42 | 96 | R | Comparative example 2 |
| 3 | 1a(100) | (R)-3 (0.5) | HCl(5) | 200 | CH$_3$OH | 10 | 99 | 96 | R | Example 1 |
| 4 | 1a(100) | (S)-3 (0.5) | HCl(5) | 200 | CH$_3$OH | 10 | 99 | 96 | S | Example 2 |
| 5 | 1a(100) | (R)-3 (0.5) | HCl(25) | 200 | CH$_3$OH | 3 | 100 | 96 | R | Example 3 |
| 6[c] | 1a(100) | (R)-3 (0.5) | HCl(5) | 200 | CH$_3$OH | 7 | 99 | 96 | R | Example 4 |
| 7 | 1a(1000) | (R)-3 (5) | HCl(250) | 200 | CH$_3$OH | 72 | 100 | 96 | R | Example 5 |
| 8[c] | 1a(100) | (R)-3 (0.1) | HCl(5) | 1000 | CH$_3$OH | 168 | 84 | 96 | R | Example 6 |
| 9 | 1a(100) | (R)-3 (0.5) | H$_2$SO$_4$(5) | 200 | CH$_3$OH | 20 | 86 | 96 | R | Example 7 |
| 10 | 1a(100) | (R)-3 (0.5) | CF$_3$SO$_3$H(5) | 200 | CH$_3$OH | 20 | 87 | 96 | R | Example 8 |

TABLE 1a-continued

| | | | | | | | Product | | | |
|---|---|---|---|---|---|---|---|---|---|---|
| No. | Substrate (mM) | Catalyst (mM) | Additive (mM) | Substrate/catalyst (mole ratio) | Solvent | Time (h) | Conversion (%) | ee (%) | Config-uration | Note |
| 11 | 1a(100) | (R)-3 (0.5) | $CH_3CO_2H$(5) | 200 | $CH_3OH$ | 20 | 27 | — | — | Example 9 |
| 12 | 1a(100) | (R)-3 (0.5) | HCl(5) | 200 | $C_2H_5OH$ | 10 | 99 | 96 | R | Example 10 |
| 13 | 1a(100) | (R)-3 (0.5) | HCl(5) | 200 | aceton | 10 | 50 | 90 | R | Example 11 |
| 14 | 1a(100) | (R)-3 (0.5) | HCl(5) | 200 | THF | 10 | 10 | — | — | Example 12 |
| 15 | 1a(100) | (R)-3 (0.5) | HCl(5) | 200 | $C_6H_6$ | 10 | 2 | — | — | Example 13 |
| 16 | 1a(100) | (R)-3 (0.5) | HCl(5) | 200 | $CH_2Cl_2$ | 10 | 10 | — | — | Example 14 |
| 17 | 1a(100) | (R)-3 (0.5) | HCl(5) | 200 | $CH_3CN$ | 10 | 1 | — | — | Example 15 |
| 18 | 1a(100) | [RuCl($C_6H_6$)(R)-binap]Cl (0.5) | HCl(5) | 200 | $CH_3OH$ | 10 | 99 | 96 | R | Example 16 |
| 19 | 1a(100) | Ru($CH_3COO$)$_2$[(R)-binap] (0.5) | — | 200 | $CH_3OH$ | 10 | 5 | — | — | Comparative example 3 |
| 20 | 1a(100) | Ru($CH_3COO$)$_2$[(R)-binap] (0.5) | HCl(5) | 200 | $CH_3OH$ | 10 | 97 | 96 | R | Example 17 |
| 21 | 1a(100) | [Rh((R)-binap)($CH_3OH$)$_2$](ClO$_4$)(0.5) | HCl(5) | 200 | $CH_3OH$ | 10 | 11 | — | — | Comparative example 4 |
| 22 | 1a(100) | RhCl((R)-binap)(cod) (0.5) | HCl(5) | 200 | $CH_3OH$ | 10 | 3 | — | — | Comparative example 5 |
| 23 | 1b(100) | (R)-3 (0.5) | HCl(25) | 200 | $CH_3OH$ | 12 | 99 | 95 | —d,e | Example 18 |
| 24 | 1c(100) | (R)-3 (0.5) | HCl(25) | 200 | $CH_3OH$ | 24 | 100 | 97 | R | Example 19 |
| 25 | 1d(100) | (R)-3 (0.5) | HCl(25) | 200 | $CH_3OH$ | 24 | 100 | 96 | R | Example 20 |
| 26 | 1e(100) | (R)-3 (0.5) | HCl(25) | 200 | $CH_3OH$ | 24 | 100 | 97 | R | Example 21 |
| 27 | 4 (100) | (R)-3 (0.5) | HCl(25) | 200 | $CH_3OH$ | 92 | 100f | 95 | R | Example 22 | aReactions were carried out under atmospheric pressure of $H_2$ at 50° C. unless otherwise specified.
bReaction under 100 atm of $H_2$.
c80° C.
dNot determined.
eThe sign of optical rotation was the same as that of sodium (R)-2-hydroxy-2-phenylethane sulfonate.
f2-Hydroxyheptadecanesulfonic acid was obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method producing an optically active β-hydroxy sulfonic acid compound comprising hydrogenating a β-keto sulfonic acid compound represented by formula 1:

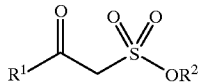

where $R^1$ represents an alkyl or a phenyl group, which may be substituted, and $R^2$ represents sodium, in an acidic solvent, in the presence of an asymmetric catalyst comprising a complex of bivalent Ru, having 2,2'-bis(diphenylphosphino)-1,1'-binaphthyl as a ligand, to produce a compound represented by formula 2:

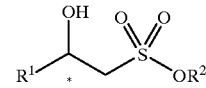

where $R^1$ and $R^2$ are as defined above, and * designates an asymmetric carbon atom.

2. The method according to claim 1, wherein said Ru complex comprises [RuCl$_2$((R) or (S)-binap)], [RuCl($C_6H_6$) ((R) or (S)-binap)]Cl, or Ru($CH_3COO$)$_2$[(R) or (S)-binap], where binap represents 2,2'-bis(diphenylphosphino)-1,1'-binaphthyl).

3. The method according to claim 1, wherein said acidic solvent is acidified with hydrochloric acid, and has a hydrochloric acid concentration in the range of 5 to 25 mmol/L.

4. The method according to claim 2, wherein said acidic solvent is acidified with hydrochloric acid, and has a hydrochloric acid concentration in the range of 5 to 25 mmol/L.

5. The method according to claim 1, wherein said solvent comprises methanol, ethanol, or acetone.

6. The method according to claim 2, wherein said solvent comprises methanol, ethanol, or acetone.

7. The method according to claim 3, wherein said solvent comprises methanol, ethanol, or acetone.

8. The method according to claim 4, wherein said solvent comprises methanol, ethanol, or acetone.

* * * * *